United States Patent
Matsui et al.

(10) Patent No.: US 10,478,063 B2
(45) Date of Patent: Nov. 19, 2019

(54) MEASUREMENT DEVICE AND MEASUREMENT METHOD

(71) Applicant: HAMAMATSU PHOTONICS K.K., Hamamatsu-shi, Shizuoka (JP)

(72) Inventors: Yoshinori Matsui, Hamamatsu (JP); Kazutaka Suzuki, Hamamatsu (JP); Haruyoshi Toyoda, Hamamatsu (JP); Munenori Takumi, Hamamatsu (JP); Naotoshi Hakamata, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 196 days.

(21) Appl. No.: 15/105,088

(22) PCT Filed: Nov. 14, 2014

(86) PCT No.: PCT/JP2014/080239
§ 371 (c)(1),
(2) Date: Jun. 16, 2016

(87) PCT Pub. No.: WO2015/093202
PCT Pub. Date: Jun. 25, 2015

(65) Prior Publication Data
US 2016/0317033 A1   Nov. 3, 2016

(30) Foreign Application Priority Data

Dec. 18, 2013 (JP) ................... 2013-261251

(51) Int. Cl.
*A61B 3/14* (2006.01)
*A61B 3/00* (2006.01)
(Continued)

(52) U.S. Cl.
CPC .............. *A61B 3/14* (2013.01); *A61B 3/0008* (2013.01); *G06K 9/00604* (2013.01); *G06T 7/73* (2017.01);
(Continued)

(58) Field of Classification Search
USPC ...... 348/78, 73, 68, 54, 50, 49, 37, 25, 269, 348/297, 342, 370, 131, 135, 137, 143,
(Continued)

(56) References Cited

U.S. PATENT DOCUMENTS

| | | | |
|---|---|---|---|
| 4,933,756 A | * | 6/1990 | Sekine ................. A61B 3/1225 348/78 |
| 5,807,273 A | * | 9/1998 | Suzuki ................. A61B 3/152 600/558 |

(Continued)

FOREIGN PATENT DOCUMENTS

| | | |
|---|---|---|
| CN | 101266647 | 9/2008 |
| CN | 102068237 | 5/2011 |

(Continued)

OTHER PUBLICATIONS

International Preliminary Report on Patentability dated Jun. 30, 2016 for PCT/JP2014/080239.

*Primary Examiner* — Brian P Yenke
(74) *Attorney, Agent, or Firm* — Drinker Biddle & Reath LLP

(57) ABSTRACT

An eyeblink measurement system 10 is a measurement apparatus for measuring a subject's eyelid position, and includes a lighting device 1 that irradiates light extending across upper to lower eyelids of the subject's eye region E, and an image measurement device 2 that has an optical axis Ia on a plane for which a plane including an irradiation optical axis La of the light is rotated by a predetermined angle θ around an axis $A_1$ along the light to be irradiated (Continued)

onto the subject, obtains height information based on the position of an optical image of the light in an image imaged, and measures the eyelid position based on the height information.

5 Claims, 16 Drawing Sheets

(51) Int. Cl.
  *G06K 9/00* (2006.01)
  *H04N 5/225* (2006.01)
  *G06T 7/73* (2017.01)

(52) U.S. Cl.
  CPC . *H04N 5/2256* (2013.01); *G06T 2207/10152* (2013.01); *G06T 2207/30196* (2013.01); *G06T 2207/30201* (2013.01)

(58) Field of Classification Search
  USPC .... 348/180, 208.3, 216.1, 333.06, 583, 687, 348/756, 759, 779, 781; 382/103, 117, 382/154; 359/508
  See application file for complete search history.

(56) References Cited

U.S. PATENT DOCUMENTS

| | | | | |
|---|---|---|---|---|
| 6,268,918 | B1* | 7/2001 | Tanabe | G01B 11/25 348/E5.029 |
| 6,832,044 | B2* | 12/2004 | Doi | A61B 3/14 348/143 |
| 8,106,783 | B2* | 1/2012 | Wada | A61B 5/02416 340/426.11 |
| 8,824,779 | B1* | 9/2014 | Smyth | G06K 9/0061 382/100 |
| 8,942,434 | B1* | 1/2015 | Karakotsios | G06K 9/00597 345/619 |
| 8,988,519 | B2* | 3/2015 | Mar | G02B 27/0093 348/76 |
| 8,998,410 | B2* | 4/2015 | Takii | A61B 3/152 351/206 |
| 9,201,512 | B1* | 12/2015 | Raffle | G06F 3/033 |
| 9,370,303 | B2* | 6/2016 | Tanaka | A61B 3/14 |
| 10,198,814 | B2* | 2/2019 | Iwase | G06T 7/0012 |
| 2002/0191075 | A1* | 12/2002 | Doi | G06K 9/00604 348/78 |
| 2005/0275749 | A1* | 12/2005 | Kojima | G03B 15/05 348/370 |
| 2008/0151186 | A1* | 6/2008 | Adachi | A61B 3/113 351/206 |
| 2008/0170238 | A1* | 7/2008 | Ochi | G01B 11/25 356/610 |
| 2008/0226175 | A1* | 9/2008 | Suzuki | G06K 9/00268 382/190 |
| 2008/0232650 | A1* | 9/2008 | Suzuki | G06K 9/00281 382/118 |
| 2009/0237208 | A1* | 9/2009 | Tsukahara | G06K 9/00604 348/78 |
| 2010/0094176 | A1* | 4/2010 | Ohue | A61B 3/14 600/595 |
| 2012/0014610 | A1* | 1/2012 | Nakashi | G06K 9/00281 382/195 |
| 2013/0093998 | A1* | 4/2013 | Bishop | A61B 3/107 351/208 |
| 2013/0101225 | A1* | 4/2013 | Kadoya | G06K 9/00597 382/199 |
| 2013/0286178 | A1* | 10/2013 | Lewis | A61B 3/113 348/78 |
| 2014/0039273 | A1* | 2/2014 | Kim | A61B 90/35 600/249 |
| 2014/0112580 | A1* | 4/2014 | Hanita | G06T 1/00 382/165 |
| 2014/0168401 | A1* | 6/2014 | De Bruijn | G06F 3/013 348/78 |
| 2014/0226002 | A1* | 8/2014 | Metzler | G01C 1/04 348/78 |
| 2014/0267668 | A1* | 9/2014 | Ignatovich | A61B 3/14 348/78 |
| 2014/0293033 | A1* | 10/2014 | Takii | A61B 3/12 348/78 |
| 2015/0009314 | A1* | 1/2015 | Sung | G06K 9/00604 348/78 |
| 2015/0138504 | A1* | 5/2015 | Korb | G06T 7/0012 351/206 |
| 2015/0169953 | A1* | 6/2015 | Border | G06F 3/03545 348/78 |
| 2015/0309567 | A1* | 10/2015 | Park | G06F 3/013 348/78 |
| 2016/0086338 | A1* | 3/2016 | Nagamatsu | G06T 7/80 348/78 |
| 2016/0302662 | A1* | 10/2016 | Suzuki | A61B 3/102 |
| 2016/0335483 | A1* | 11/2016 | Pfursich | G06K 9/00899 |
| 2018/0004287 | A1* | 1/2018 | Yoo | G06T 7/248 |
| 2018/0125357 | A1* | 5/2018 | Suzuki | A61B 3/113 |
| 2018/0144663 | A1* | 5/2018 | Kirchoff | G09B 23/32 |
| 2018/0164595 | A1* | 6/2018 | Arakawa | G09G 5/00 |

FOREIGN PATENT DOCUMENTS

| | | |
|---|---|---|
| CN | 102375974 | 3/2012 |
| CN | 102752458 | 10/2012 |
| JP | S59-186538 A | 10/1984 |
| JP | H07-313459 A | 12/1995 |
| JP | 2000-102510 A | 4/2000 |
| JP | 2000-157493 A | 6/2000 |
| JP | 2007-257332 | 10/2007 |
| JP | 2007-531579 A | 11/2007 |
| JP | 2008-226047 A | 9/2008 |
| JP | 2010-273954 A | 12/2010 |

* cited by examiner (a)

(b)

(a)

(b)

MEASUREMENT DEVICE AND MEASUREMENT METHOD

TECHNICAL FIELD

The present invention relates to a measurement apparatus and a measurement method for measuring a subject's eyelid position.

BACKGROUND ART

Conventionally, development of measurement methods for the purpose of, for example, diagnosing various diseases by measuring a subject's eye movement has been advanced. For example, with the apparatus described, in the following patent document 1, a subject's eye image obtained by a camera is observed as a target for changes in density value in the up-down direction, and an eyelid position is measured by using that the density value changes between the eyelid and eyeball. Also, with the apparatus described in the following patent document 2, a subject moving image is obtained by a camera, and an edge line to serve as a candidate for a combination of the upper and lower eyelids is extracted based on the brightness/darkness of the moving image, and with the apparatus described in the following patent document 3, a one-dimensional image showing a gray scale variation is extracted based on a luminance distribution from a subject's eye image, and a boundary point between the eyelid and eyeball is detected based on the one-dimensional image. Also, with the apparatus described in the following patent document 4, the intensity of reflected light and scattered light of light caused to strike a subject's eye is detected by a sensor to thereby generate a signal indicating whether the eyelid is in an open state or a closed state.

CITATION LIST

Patent Literature

Patent Document 1: Japanese Unexamined Patent Publication No. 2000-102510
Patent Document 2: Japanese Unexamined Patent Publication No. 2008-226047
Patent Document 3: Japanese Unexamined Patent Publication No. H7-313459
Patent Document 4: Japanese Unexamined Patent Publication No. 2007-531579

SUMMARY OF INVENTION

Technical Problem

However, with measurement methods in the apparatuses described in patent documents 1 to 3 described above, when measuring an eyelid position based on a change in luminance value, a precise measurement of the eyelid position has tended to be difficult due to the influence of disturbance light or the influence of eyelashes. With the apparatus described in patent document 4, because the intensity of reflected light and scattered light variously changes due to the influence of a skin condition, makeup, etc., it is difficult to precisely measure the eyelid position. Also, this apparatus has a lower precision because the influence of a scattered light component due to eyelashes is included during measurement.

Therefore, the present invention has been made in view of such problems, and an object thereof is to provide a measurement apparatus and a measurement method capable of more precisely measuring a subject's eyelid position.

Solution to Problem

In order to solve the above-mentioned problems, a measurement apparatus according to a mode of the present invention is a measurement apparatus for measuring a subject's eyelid position, and includes a lighting section that irradiates light extending across the subject's upper to lower eyelids, an imaging device having an optical axis on a plane for which a plane including an optical axis of the light is rotated by a predetermined angle around an axis along the light to be irradiated onto the subject, and an arithmetic section that obtains height information based on a position of an optical image in an image imaged by the imaging device, and measures the eyelid position based on the height information.

Or, a measurement method according to another mode of the present invention is a measurement method for measuring a subject's eyelid position, and includes an illuminating step of irradiating light extending across the subject's upper to lower eyelids, an imaging step of setting an imaging optical axis on a plane for which a plane including an optical axis of the light is rotated by a predetermined angle around an axis along the light to be irradiated onto the subject, and obtaining an image of the subject, and an arithmetic step of obtaining height information based on a position of an optical image in the image obtained in the imaging step, and measuring the eyelid position based on the height information.

By such a measurement apparatus or measurement method, a subject's image is obtained with the imaging optical axis set that is rotated by the predetermined angle with respect to the light to be irradiated onto the upper to lower eyelids by the lighting section, height information is obtained based on the position of an optical image in this image, and an eyelid position is measured based on the height information. As a result, the influence of disturbance light and the influence of eyelashes or the influence of intensity changes of reflected light and scattered light due to a skin condition, makeup, etc., is unlikely to be received, and a more precise measurement of the eyelid position becomes possible.

Advantageous Effects of Invention

According to the present invention, a subject's eyelid position can be more precisely detected.

DESCRIPTION OF EMBODIMENTS

Figure 1:
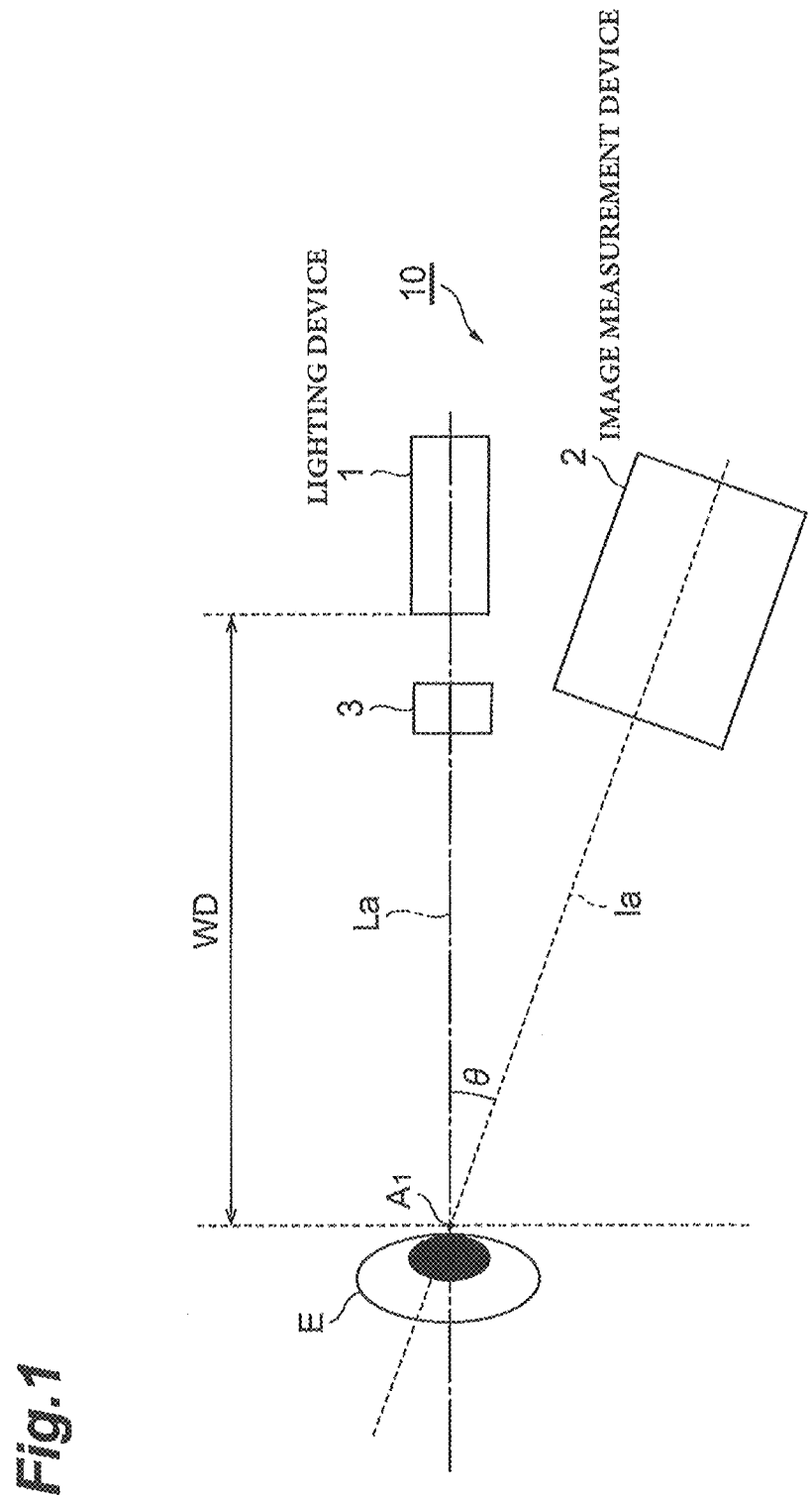
FIG. 1 is a plan view showing a schematic configuration of an eyeblink measurement system which is a measurement apparatus according to a preferred embodiment of the present invention.

Hereinafter, an embodiment of a measurement apparatus and a measurement method according to the present invention will be described in detail with reference to the accompanying drawings. In addition, the same components will be denoted by the same reference signs in the description of the drawings, and overlapping description will be omitted. Also, the respective drawings are prepared for the purpose of description, and are drawn so that the portions to be described are especially emphasized. Therefore, the dimensional ratios of the respective members in the drawings are not always coincident with actual ratios.

FIG. 1 is a plan view showing a schematic configuration of an eyeblink measurement system 10 which is a measurement apparatus according to a preferred embodiment of the present invention. In the same figure, a positional relationship of respective components of the eyeblink measurement system 10 viewed from above a subject's head is shown. This eyeblink measurement system 10 is a measurement system that is disposed so as to face a region E including the subject's eye and measures the subject's eyelid position in time series to obtain parameters concerning the subject's blinking, and is constructed including a lighting device (lighting section) 1 that irradiates light, a filter 3 disposed between the lighting device 1 and the subject's region E, and an image measurement device 2 that processes image data obtained by imaging an optical image in the region E.

Figure 2:
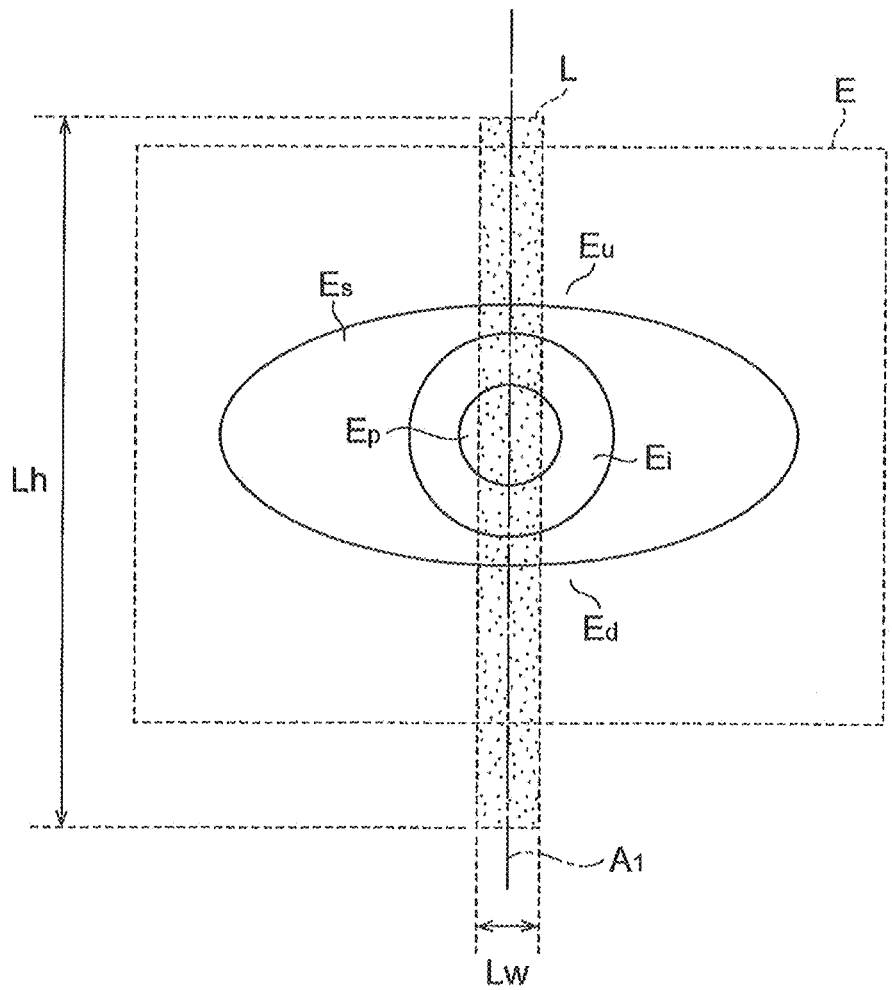
FIG. 2 is a front view showing an illumination state by the lighting device 1 in FIG. 1 in a subject's region E.

The lighting device 1 is a light source that is disposed so as to directly oppose the subject's region E and irradiates light extending across the subject's upper to lower eyelids. For example, the lighting device 1 irradiates a band-like line light across the subject's upper to lower eyelids. FIG. 2 is a front view showing an illumination state by the lighting device 1 in the subject's region E. As shown in the same figure, the lighting device 1 irradiates the region E including an eye having an upper eyelid $E_u$, a lower eyelid $E_d$, a pupil $E_p$, a sclera (white) $E_s$, and an iris $E_i$ as a target, with such a light L of a width Lw so as to vertically cross the same linearly in a range of a length Lh including the upper eyelid $E_u$ to the lower eyelid $E_d$. That is, the lighting device 1 has an irradiation optical axis La on a plane including a light emission center of the lighting device 1 and the subject's region E, and generates a light L that is irradiated from the subject's upper eyelid $E_u$ to the lower eyelid $E_d$. Here, for the lighting device 1, the values of the length Lh and the width Lw are adjusted so as to become values optimal for measurement, respectively, and particularly, the value of the width Lw of a light L to be irradiated is adjusted so as to become not less than 0.1 mm, which is an average thickness of human eyelashes. Also, the lighting device 1 is disposed so that its light emission center is away from the subject's region E by a distance WD. The distance WD is set so as to be coincident with a working distance previously specified regarding the lighting device 1 so that the width Lw of a light L to be irradiated onto the region E becomes the narrowest. On the other hand, in order to adjust the width Lw of the light L to be irradiated onto the region E, the lighting device 1 may be disposed by moving it so as to increase or reduce its distance WD in an arbitrary range from the working distance.

Such a lighting device 1 is constituted of, for example, a light source such as an LD (Laser Diode) or an SLD (Super Luminescent Diode) and lenses including a cylindrical lens, a collimating lens, etc., but may be constituted of an LED (Light-Emitting Diode) and a slit plate as long as the above-mentioned conditions are satisfied. Also, the emission wavelength of the lighting device 1 is preferably a wavelength in a near-infrared region or infrared region being an invisible wavelength region in order to suppress the effect on an eye blinking motion due to a sense of blinding or discomfort as a result of the subject's directly perceiving light, and is set to a wavelength region of, for example, 750 nm or more. Further, the emission intensity of the lighting device 1 is set to a sufficiently small value from the point of view of protecting the subject's eye.

Referring back to FIG. 1, the filter 3 is an ND (Neutral Density) filter, disposed so as to pass a bundle of rays generated by the lighting device 1, for performing adjustment of the intensity of a light L to be irradiated onto the subject for the purpose of protecting the subject's eye. The filter 3 may be a single filter, or may be a combination of a plurality of filters.

The image measurement device 2 is constructed so as to have its imaging optical axis Ia on a plane for which a vertical plane (plane along the bundle of rays) including the irradiation optical axis La is rotated by a predetermined angle θ around an axis $A_1$ along a light L to be irradiated onto the eye region E. That is, the image measurement device 2 has its imaging optical axis Ia set on a plane including an axis for which the irradiation optical axis La is rotated by the angle θ, and images the region E from a direction oblique to a directly opposite direction.

Figure 3:
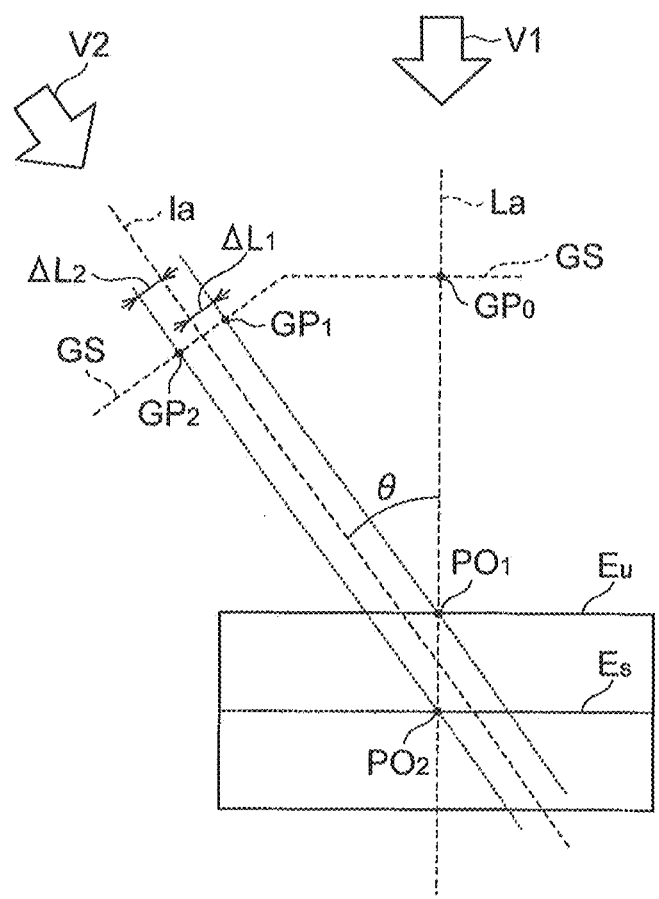
FIG. 3 is a horizontal sectional view showing how optical images at an eyelid and white in the region E are viewed depending on the arrangement position of an image measurement device 2 with respect to the lighting device 1.
Figure 4:
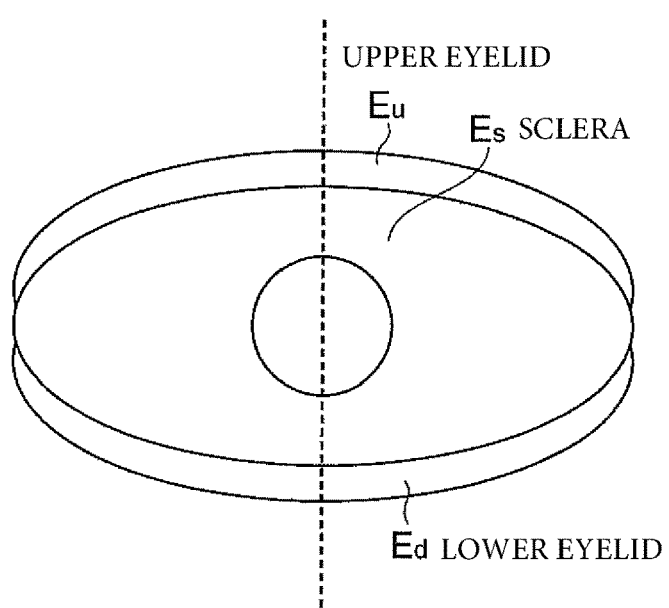
FIG. 4 includes views showing picture images in the region E depending on the arrangement position of an image measurement device 2 with respect to the lighting device 1.
Figure 4:
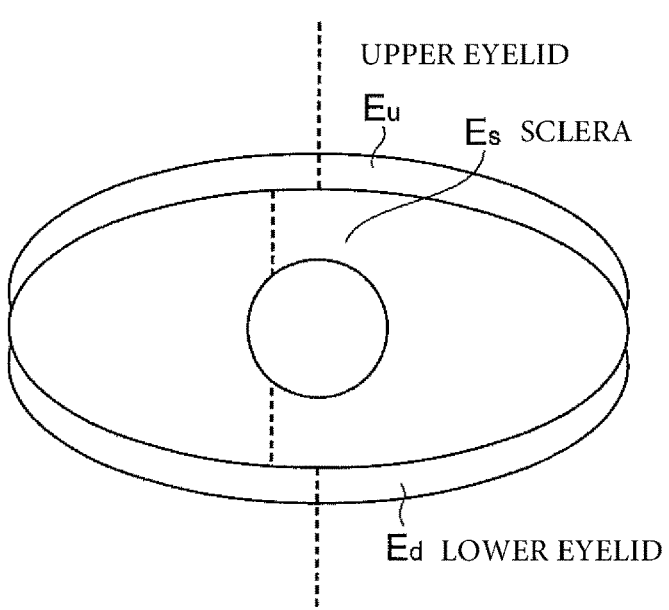

FIG. 3 is a horizontal sectional view showing how optical images at the eyelid $E_u$ and the white $E_s$ in the region E are viewed depending on the arrangement position of the image measurement device 2 with respect to the lighting device 1, and FIG. 4 includes views showing picture images in the region E depending on the arrangement position of the image measurement device 2 with respect to the lighting device 1.

As shown in FIG. 3, the imaging optical axis Ia is rotated by the angle θ with respect to the irradiation optical axis La. Therefore, with respect to a line of vision V1 to view an irradiation position of a light L in the region E from the position of the lighting device 1, a line of vision V2 to view the irradiation position of the light L in the region E from the position of the image measurement device 2 is also rotated by the angle θ. In FIG. 3, because the eyelid $E_u$ exists positionally ahead of the white $E_s$, in the region E, a scattering position $PO_1$ of the light L at the eyelid $E_u$ that exists on the irradiation optical axis La is located in front of a scattering position $PO_2$ of the light L at the white $E_s$ that exists on the irradiation optical axis La. At this time, when the image measurement device 2 is installed coaxially with the lighting device 1, that is, when the image measurement device 2 is installed on the irradiation optical axis La, the image measurement device 2 views an irradiation part with the light L along the line of vision V1. In this case, because the imaging optical axis Ia and the irradiation optical axis La coaxially exist, the projection positions of optical images on an image plane GS due to scattered light components from the two positions $PO_1$ and $PO_2$ both result in $GP_0$ and are thus coincident. On the other hand, when the image measurement device 2 is installed in a manner rotated by the angle θ with respect to the lighting device 1, the image measurement device 2 views an irradiation part with the light L along the line of vision V2. In this case, the projection position of an optical image on an image plane GS due to a scattered light component from the position $PO_1$ results in $GP_1$, which is a rightward shift from a center position of the image plane GS by a linear distance $\Delta L_1$ that is geometrically calculated from the angle θ created by the imaging optical axis Ia and the irradiation optical axis La. Similarly, the projection position of an optical image on an image plane GS due to a scattered light component from the position $PO_2$ results in $GP_2$, which is a leftward shift from a center position of the image plane GS by a linear distance $\Delta L_2$ that is geometrically calculated from the angle θ created by the imaging optical axis Ia and the irradiation optical axis La. That is, an amount of mismatch of the projection position in the image plane GS of an optical image imaged by the image measurement device 2 installed at a position rotated horizontally by the angle θ from the lighting device 1 represents a height difference of the eyelid $E_u$ and the white $E_s$ in the region E.

Concretely, as shown in the part (a) of FIG. 4, in an image that is obtained when the imaging optical axis Ia is present coaxially with the irradiation optical axis La, optical images due to scattered light components from the respective parts of the eyelids $E_u$ and $E_d$ and the white $E_s$ that exist at a part irradiated with the light L in the region E all exist on an identical straight line. On the other hand, as in the present embodiment shown in the part (b) of FIG. 4, in an image that is obtained when the imaging optical axis Ia is rotated horizontally by the angle θ with respect to the irradiation optical axis La, optical images due to scattered light components from the respective parts of the eyelids $E_u$ and $E_d$ and the white $E_s$ that exist at a part irradiated with the light L in the region E have a shift (mismatch) by an amount according to a height difference at each boundary part between the eyelid $E_u$, $E_d$ and the white $E_s$. In greater detail, when the imaging optical axis Ia is rotated counterclockwise by the angle θ with respect to the irradiation optical axis La, the position of an optical image due to a scattered light component of the light L at the white $E_s$ is shifted (mismatched) to a horizontally left side in an image plane with respect to the position of an optical image due to a scattered light component of the light L at the eyelid $E_u$, $E_d$. The shift amount is proportional to the height difference of the eyelid $E_u$, $E_d$ and the white $E_s$. Therefore, by obtaining the shift amount in subpixel units not more than one pixel of image data, height information in the region E can be obtained at a high accuracy.

Figure 5:
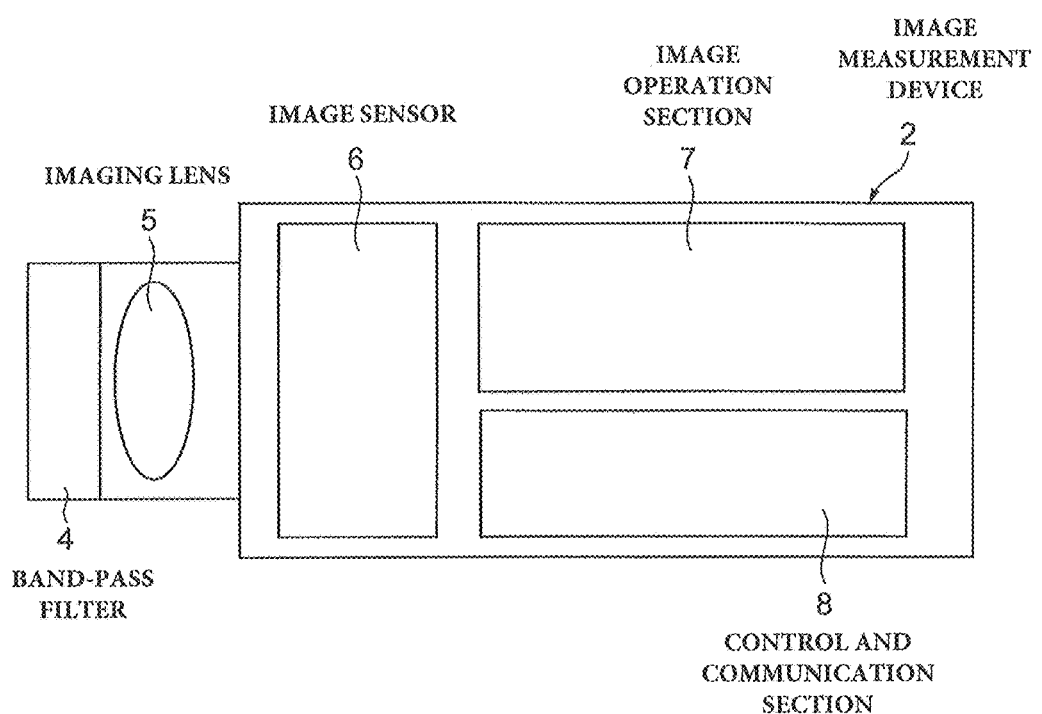
FIG. 5 is a schematic configuration view showing a detailed configuration of the image measurement device 2 in FIG. 1.

Next, referring to FIG. 5, a detailed configuration of the image measurement device 2 will be described.

As shown in the same figure, the image measurement device 2 is constituted of an imaging lens 5, an image sensor (imaging device) 6, an image operation section 7, and a control and communication section 8. The imaging lens 5 has an angle of view covering the region E including from the subject's upper eyelid $E_u$ to the lower eyelid $E_d$, and condenses a reflected light and scattered light component of the light L irradiated by the lighting device 1 to form an image on the image sensor 6. The image sensor 6 photoelectrically converts pixel by pixel the reflected light component and scattered light component condensed by the imaging lens 5 to thereby generate in time series an image signal (electrical signal) representing a two-dimensional distribution of the luminance of an optical image on an image plane. Also, the image sensor 6 transfers the generated image signal to the image operation section 7. The image operation section 7 performs image processing for the image signal generated by the image sensor 6, obtains height information along the horizontal direction (irradiation direction of the light L) in the subject's region E, and further measures the subject's eyelid position based on the height information. Concretely, the image operation section 7 executes a smoothing processing, a one-dimensional centroid calculation processing, an adjacent pixel subtraction processing, etc., for the image signal, obtains height information and luminance information at an irradiation position of the light L, and performs eyelid position detection based on the information. The control and communication section 8 controls the operation of the image sensor 6 and the image operation section 7, and also transmits an operation result by the image operation section 7 to the outside. Examples of a device constituting such an image measurement device 2 that can be mentioned include an intelligent vision system (IVS) manufactured by Hamamatsu Photonics K.K. that includes a high-speed two-dimensional CMOS sensor and a high-speed parallel image processing mechanism. In addition, the imaging lens 5 may be mounted with a band-pass filter 4 that passes only an emission wavelength of the lighting device 1 and blocks a wavelength range excluding the emission wavelength in order to suppress the influence on measurement due to disturbance light. The band-pass filter 4 may be a single filter, or may be a combination of a plurality of filters.

Figure 6:
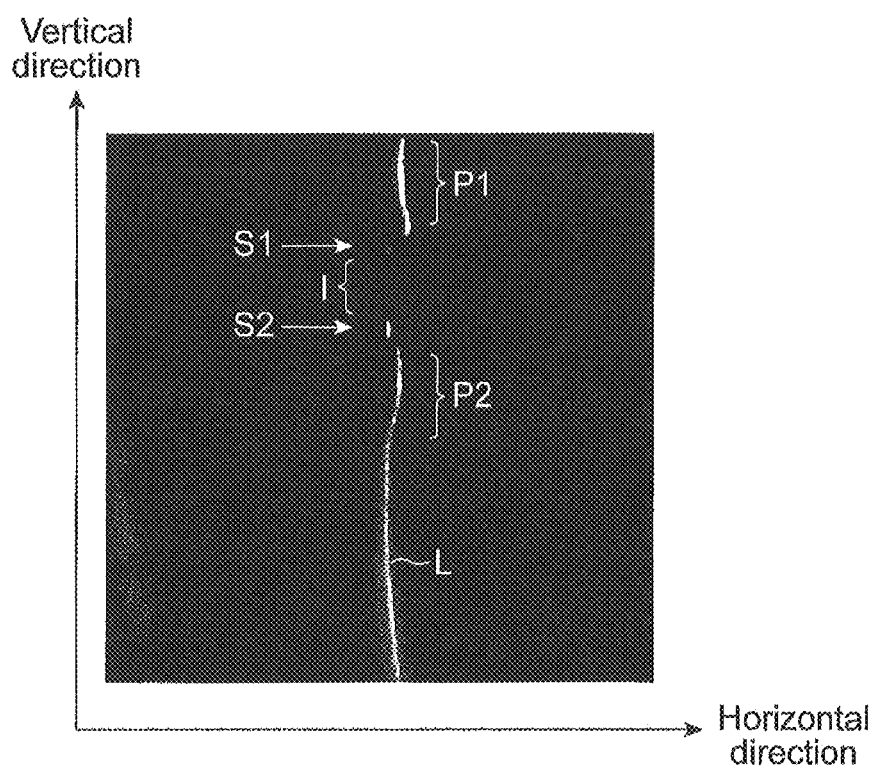
FIG. 6 is a view showing an example of image data imaged at the time of eyelid opening of a subject by the image measurement device 2 in FIG. 1.
Figure 7:
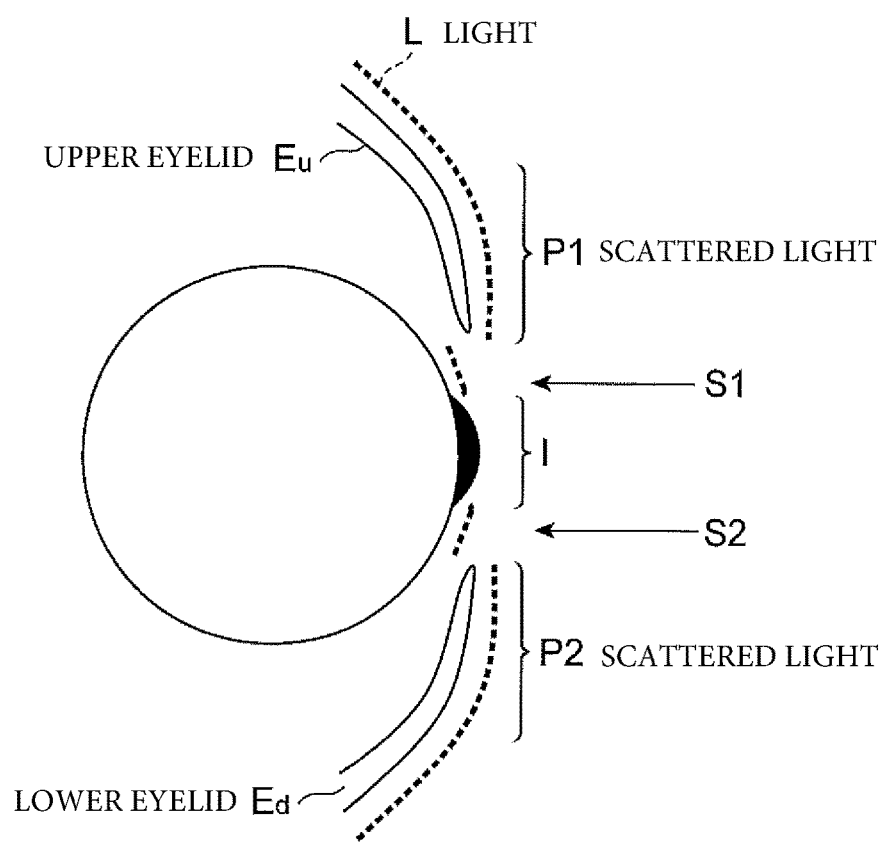
FIG. 7 is a sectional view viewed laterally of the region E at the time of eyelid opening of a subject.

FIG. 6 shows an example of image data imaged at the time of eyelid opening of a subject by the image measurement device 2, and FIG. 7 shows a sectional view viewed laterally of the subject's region E at this time. As shown in FIG. 7, a band-like light L is irradiated extending over the upper eyelid $E_u$, the lower eyelid $E_d$, and the white and iris parts of the eyeball. At this time, as shown in FIG. 6, scattered lights P1 and P2 at the upper eyelid E and the lower eyelid $E_d$ and scattered lights S1 and S2 at the white $E_s$ appear on the image data. The positions on the image data of the scattered lights S1 and S2 are shifted leftward with respect to the scattered lights P1 and P2 according to height differences of the eyelids $E_u$ and $E_d$ and the white $E_s$, respectively. In addition, because the intensity of a scattered light component at the iris part is relatively weak as compared with that at the white part, a scattered light I of the iris part does not appear on the image data shown in FIG. 6.

Figure 8:
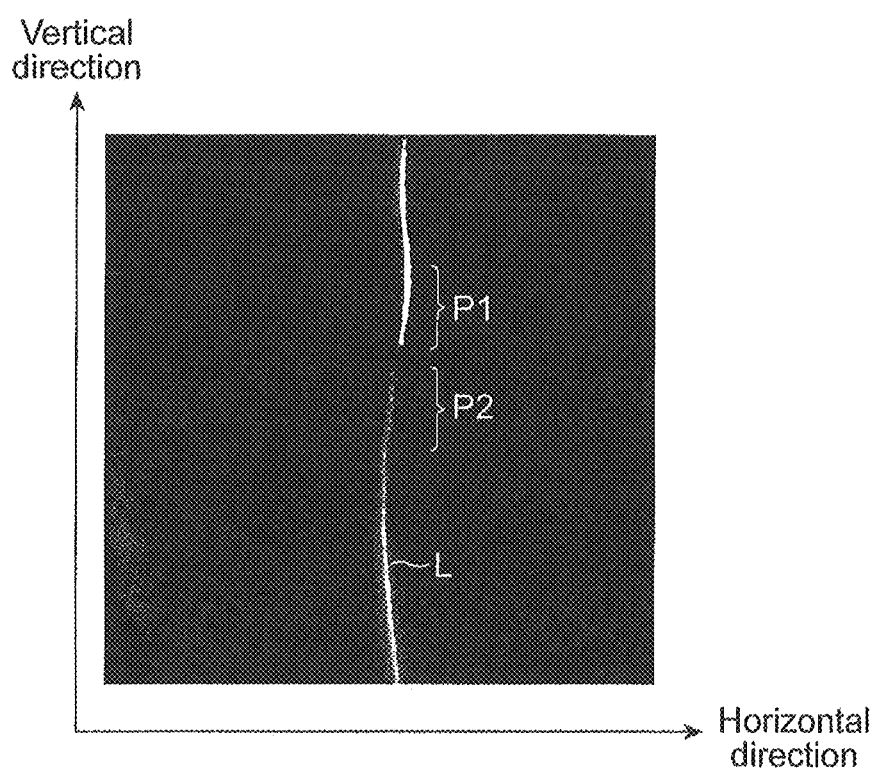
FIG. 8 is a view showing an example of image data imaged at the time of eyelid closure of a subject by the image measurement device 2 in FIG. 1.
Figure 9:
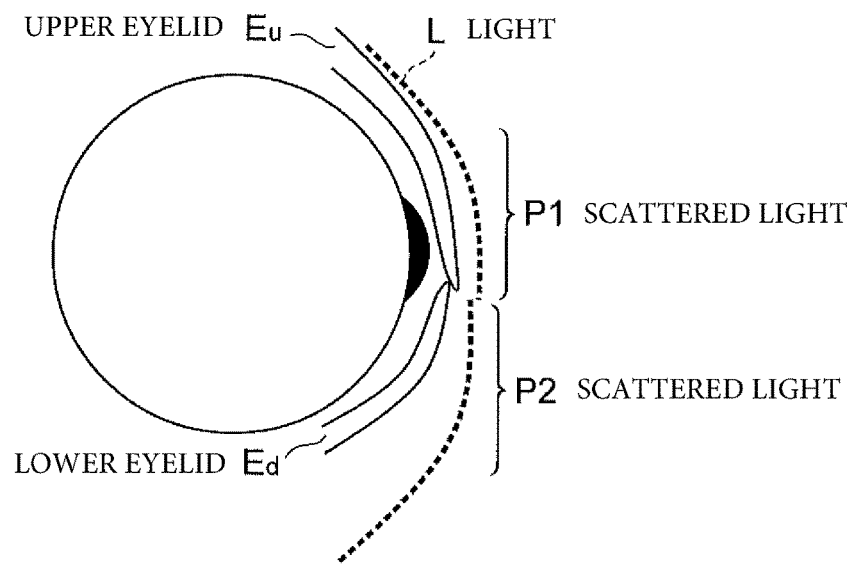
FIG. 9 is a sectional view viewed laterally of the region E at the time of eyelid closure of a subject.

Also, FIG. 8 shows an example of image data imaged at the time of eyelid closure of a subject by the image measurement device 2, and FIG. 9 shows a sectional view viewed laterally of the subject's region E at this time. As shown in FIG. 9, the light L is irradiated in a state of the upper eyelid $E_u$ stretching due to eyelid closure to overlap the lower eyelid $E_d$. At this time, as shown in FIG. 8, scattered lights P1 and P2 at the upper eyelid $E_u$ and the lower eyelid $E_d$ appear on the image data. At the time of eyelid closure, the upper eyelid $E_u$ is partially laid over the lower eyelid $E_d$, a height difference occurs between the scattered lights P1 and P2. Consequently, the position on the image data of the scattered light P2 is shifted leftward by a movement amount according to a height difference from the scattered light P1.

By using such properties, the image operation section 7 of the image measurement device 2 obtains a positional mismatch of an optical image of the light L in a direction perpendicular to a direction in which the light L extends, that is, in the horizontal direction, and can thereby obtain height difference information of the eyeball part and eyelid part both at the time of eyelid opening and at the time of eyelid closure. Further, the image operation section 7, based on the obtained height difference information of the eyeball part and eyelid part, estimates an eyelid position from a height changing point between the eyeball and the upper or lower eyelid at the time of eyelid opening, and at the time of eyelid closure, estimates an eyelid position from a height changing point between the upper and lower eyelids.

The procedure of an eyelid position estimation processing by the image measurement device 2 will be described in greater detail. First, the light L is irradiated onto the subject's region E with the region E made directly opposite the lighting device 1. The region E is imaged in this state by the image measurement device 2, and image data is obtained in time series to generate time-series image data. Thereafter, an estimation processing of the eyelid position is executed for the time-series image data by the image operation section 7 of the image measurement device 2. Concretely, the image operation section 7, by performing a one-dimensional centroid calculation laterally (horizontally) for the image data, obtains a precise lateral position of an optical image of the light L. The image operation section 7 then obtains, from the lateral position of the optical image of the light L obtained by the one-dimensional centroid calculation, a lateral shift amount of the optical image, that is, height difference information. Further, the image operation section 7, by successively processing the time-series image data, determines a temporal change in height difference information. The image operation section 7 then estimates an eyelid position from a change in height difference information in the longitudinal direction (vertical direction), and obtains a temporal positional change in the eyelid position. In addition, the iris part of the region E has a scattered light component intensity that is relatively weak as compared with that of the white part, and therefore may not become a calculation target depending on a threshold setting at the time of a one-dimensional centroid calculation. In that case, the value of height difference information at said part is provided as zero.

Figure 10:
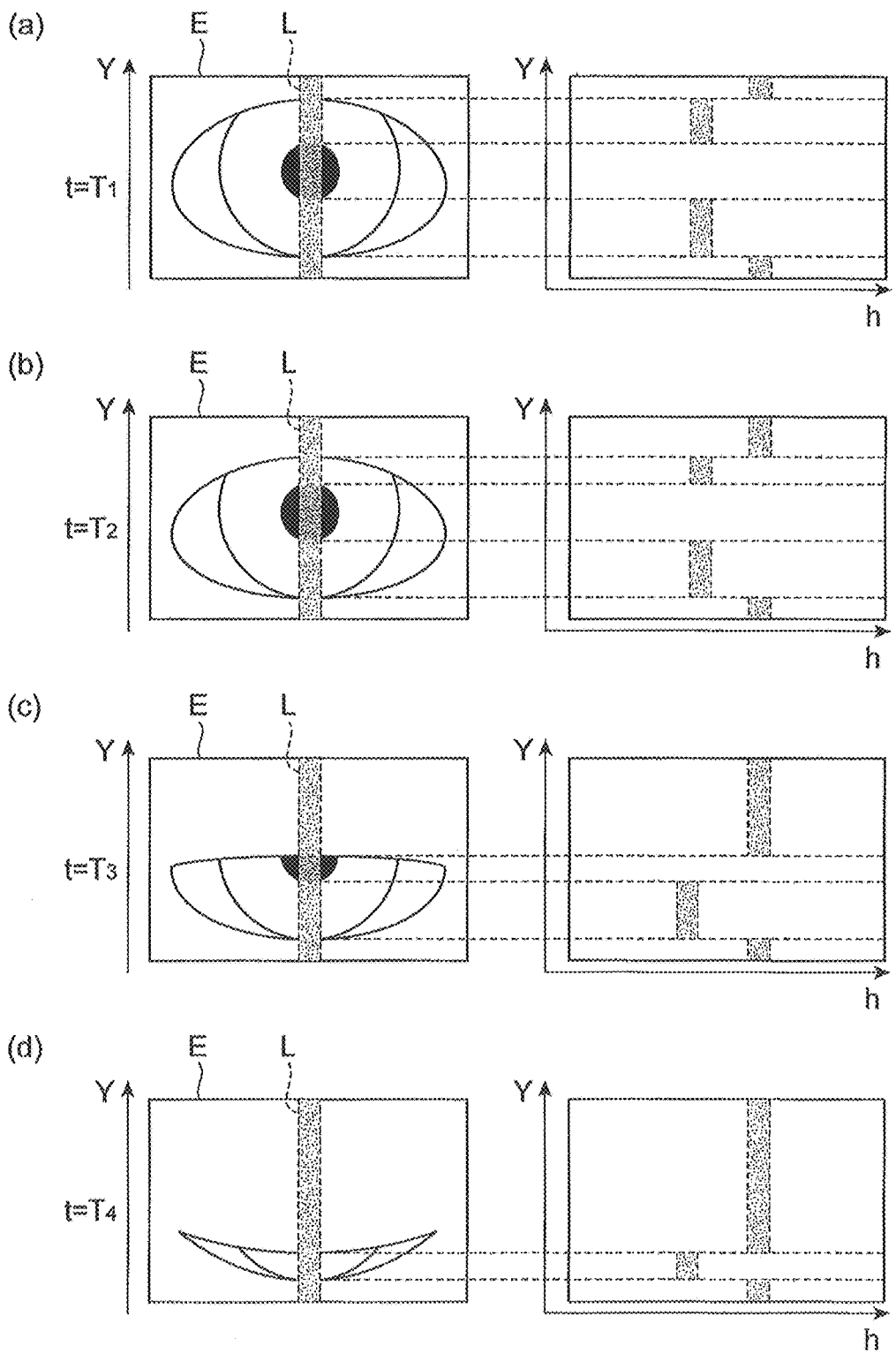
FIG. 10 includes views showing an example of time-series image data to be processed by the image operation section 7 in FIG. 5.

FIG. 10 shows an example of time-series image data to be processed by the image operation section 7. In each of parts (a)-(d) of the same figure, irradiation states of a light L in the region E are shown in time series (time $t=T_1<T_2<T_3<T_4$) at the left side, and at the right side, shown are optical images of the light L on image data obtained by the image measurement device 2 correspondingly to the respective irradiation states. As shown in the same figure, it can be understood that while it transitions from an eyelid opening state ($t=T_1$) to an eyelid closure state ($t=T_4$), a changing point in the longitudinal direction Y (vertical direction) of an optical image shift of the light L that appears at a boundary between the upper eyelid and white moves downward. In addition, scattered lights from the periphery of the eye, eyelashes, and eyebrow sometimes exist as a background on image data, but in this image data example, only the optical images of the light L are shown for the purpose of illustration. The image operation section 7 measures an upper eyelid position by determining a changing point of shifting of the light L, and analyzes an eye blinking motion from a temporal change in the upper eyelid position.

Figure 11:
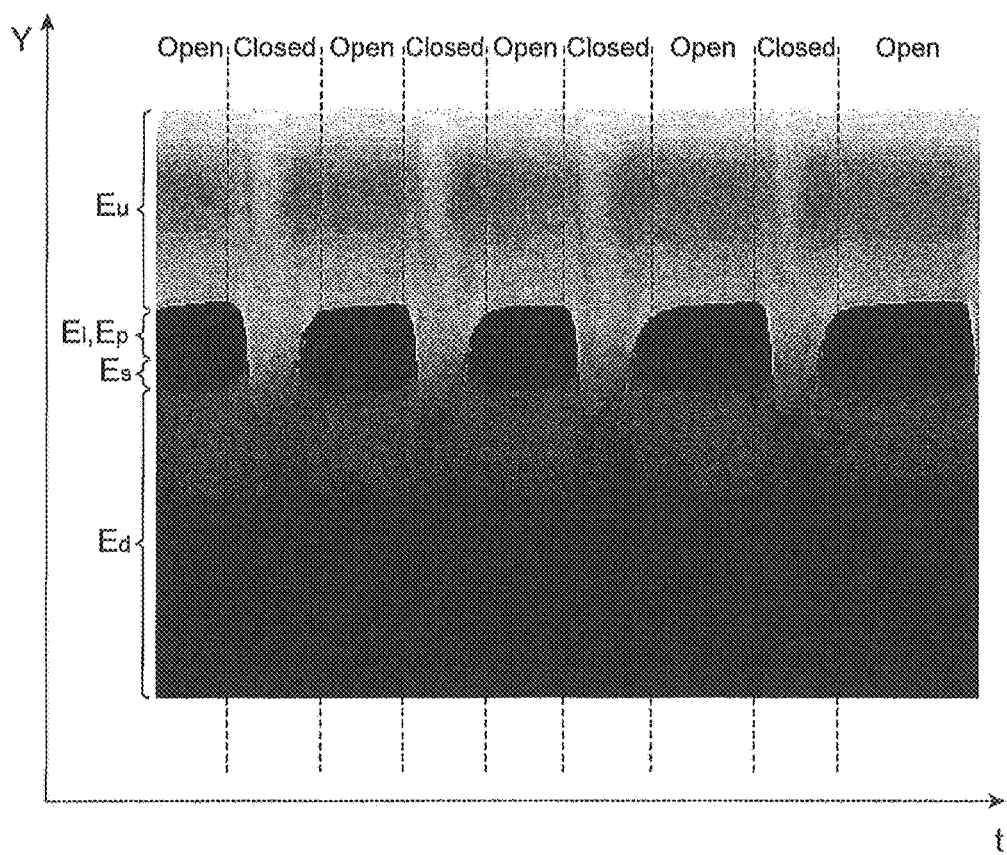
FIG. 11 is a graph showing a result of a one-dimensional centroid calculation performed by the image operation section 7 for time-series image data imaged by the image measurement device 2 in FIG. 5.

FIG. 11 shows a result of a one-dimensional centroid calculation performed by the image operation section 7 for time-series image data imaged by the image measurement device 2. In the same figure, height differences are represented by tones, and which indicates that the closer to white, the higher the height, and the closer to black, the lower the height. The horizontal axis (t) is a time axis, and a measurement was performed for about four seconds to measure about four times of opening and closing of eyelids. According to the result in the same figure, at the time of eyelid opening (sites denoted by "open" in the figure), between the upper eyelid part $E_u$ and the iris part $E_i$, $E_p$ and the white part $E_s$, there are clear differences in the tones representing height differences of the respective portions. The image operation section 7 further takes differences between adjacent pixels in the longitudinal direction (Y) from this result, and obtains the position where a change in the difference value greatly changes in the longitudinal direction as an upper eyelid position. Also at the time of eyelid closure (sites denoted by "closed" in the figure), because there are differences in the tones between the upper eyelid part $E_u$ and the lower eyelid part $E_d$, the image operation section 7 takes differences between adjacent pixels in the longitudinal direction, and obtains the position where the difference value greatly changes as a boundary position between the upper and lower eyelids.

Figure 12:
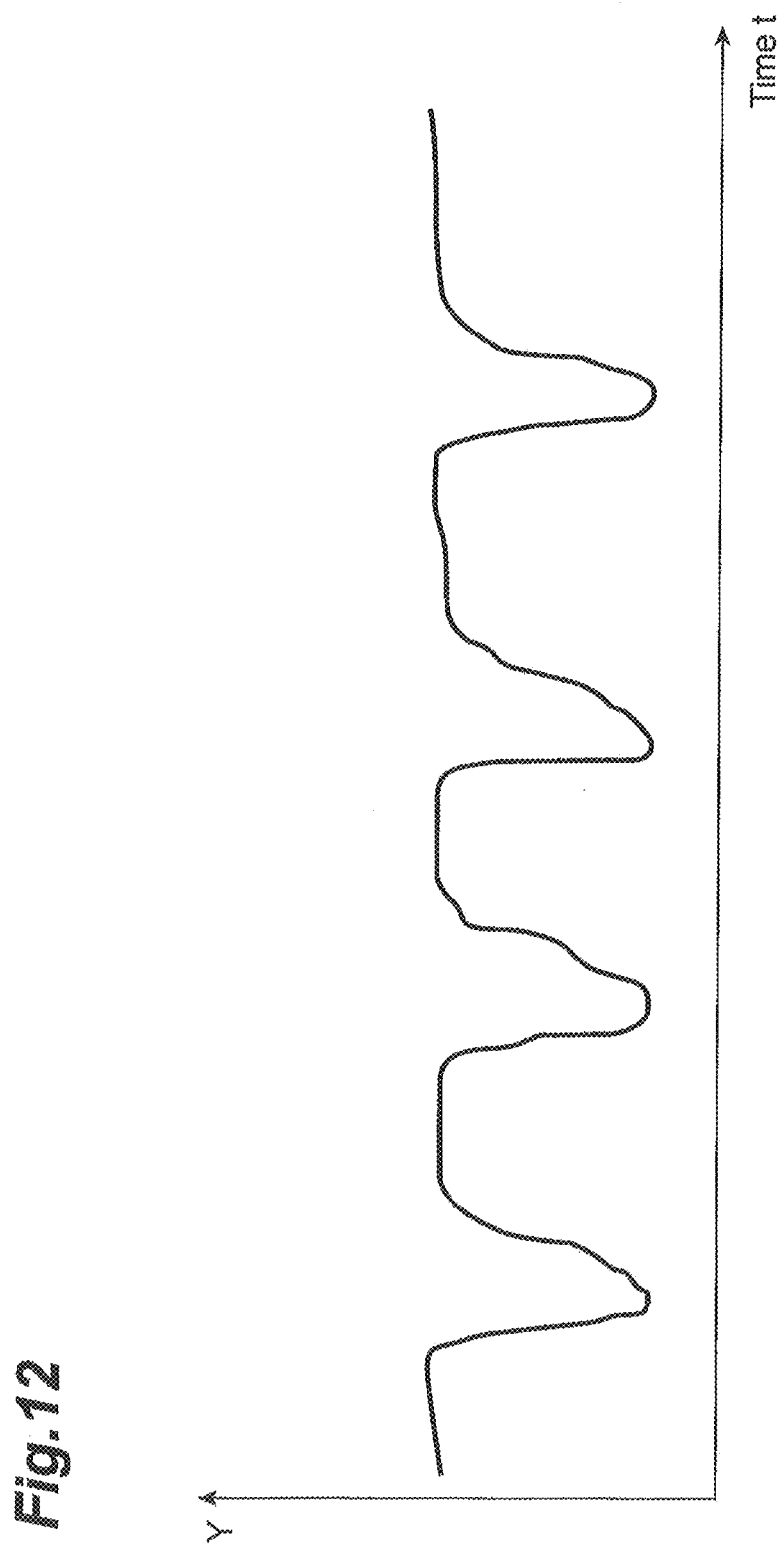
FIG. 12 is a graph showing an example of temporal changes in the boundary position of an upper eyelid obtained by the image operation section 7 in FIG. 5.

Further, FIG. 12 shows an example of temporal changes in the boundary position of the upper eyelid obtained by the image operation section 7 in the manner as above. It becomes possible to obtain, from thus obtained data, parameters such as an eye opening speed, an eye closing speed, and an eye closing time of the subject's blinking.

By the eyeblink measurement system 10 or the measurement method using the same having been described above, a subject's image is obtained with the imaging optical axis Ia set that is inclined by the angle θ with respect to the irradiation optical axis La of the light L to be irradiated onto the subject's upper to lower eyelids by the lighting device 1, height difference information is obtained based on the position of an optical image of scattered light of the light L in this image, and an eyelid position is measured based on the height information. As a result, the influence of the generation of scattered light at the eyelid and the like, the influence of eyelashes, or the influence of variation in scattering conditions is unlikely to be received, and a more precise measurement of the eyelid position becomes possible. Thereby, an accurate analysis of the subject's eye blinking motion is realized.

Here, because the image operation section 7 of the image measurement device 2 obtains height information of the region E along the irradiation direction of the light L based on the position of an optical image of the light L in a direction perpendicular to a direction in which the optical image extends, a relative height of the subject's upper to lower eyelids is accurately detected, and the subject's eyelid position can as a result be measured more precisely.

Also, the lighting device 1 is disposed along the irradiation optical axis La so as to directly oppose the subject, and the image measurement device 2 is disposed along the imaging optical axis Ia rotated by the angle θ from the irradiation optical axis La. By such an arrangement configuration, a relative height of the subject's upper to lower eyelids can be accurately detected.

However, the present invention is not limited to the embodiment described above. For example, the light L to be irradiated from the lighting device 1 is not particularly limited in its shape as long as it is light extending across a subject's upper to lower eyelids, and may be, for example, in a rectangular shape or in a trapezoidal shape. In this regard, if it is a band-like line light, height information is easily obtained based on the position of an optical image obtained by the image measurement device 2, so that the measurement accuracy is improved.

Also, the lighting device 1 and the image measurement device 2 can be variously changed in their arrangement relationship.

Figure 13:
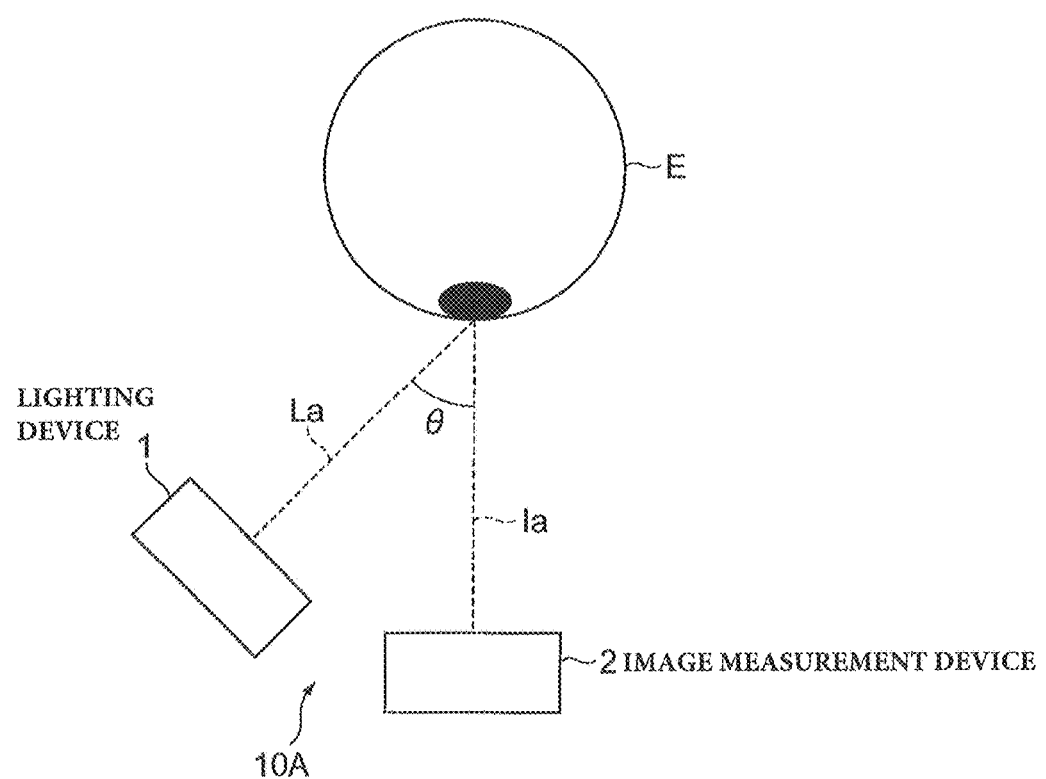
FIG. 13 is a schematic configuration view showing an arrangement relationship of an eyeblink measurement system 10A according to a modification of the present invention.

FIG. 13 is a schematic configuration view showing an arrangement relationship of an eyeblink measurement system 10A according to a modification of the present invention. In the eyeblink measurement system 10A shown in the same figure, the image measurement device 2 is disposed along the imaging optical axis Ia so as to directly oppose the subject's region E, and the image measurement device 2 is arranged so as to be disposed along the imaging optical axis Ia rotated by the angle θ from the irradiation optical axis La of the irradiation device 1. Also by such an arrangement, height difference information in the region E can be obtained based on the position of an optical image of the light L irradiated onto the region E, so that a relative height of the subject's upper to lower eyelids can be accurately detected.

Figure 14:
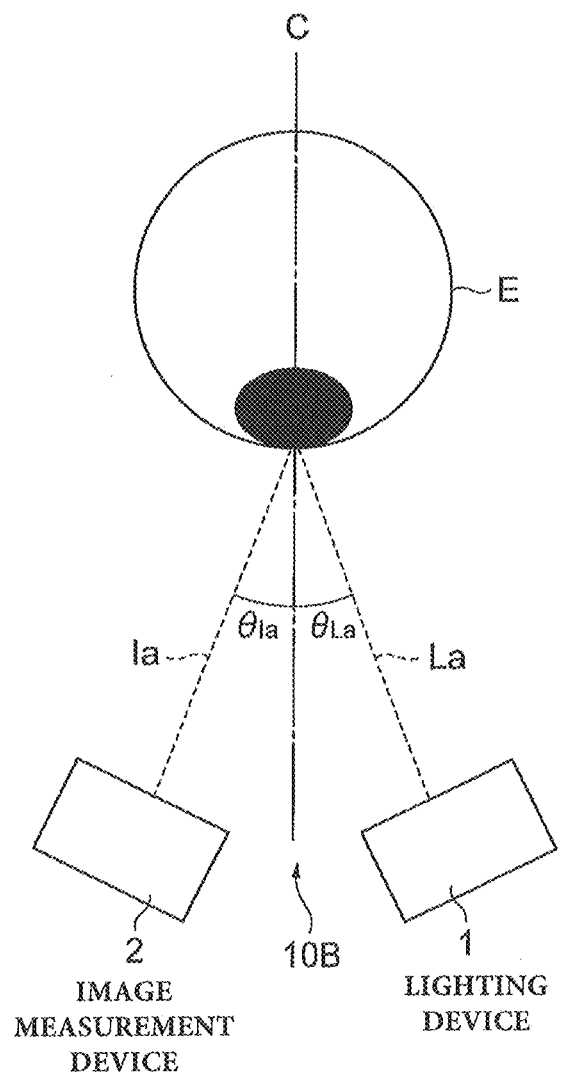
FIG. 14 is a schematic configuration view showing an arrangement relationship of an eyeblink measurement system 10B according to another modification of the present invention.

Also, FIG. 14 is a schematic configuration view showing an arrangement relationship of an eyeblink measurement system 10B according to another modification of the present invention. In the eyeblink measurement system 10B shown in the same figure, the lighting device 1 is installed along the irradiation optical axis La rotated by an angle $\theta_{La}$ with respect to a center line C in the subject's region E. Also, the image measurement device 2 is installed along the imaging optical axis Ia rotated by an angle $\theta_{Ia}$ with respect to the center line C in the subject's region E. Also by such an arrangement, height difference information in the region E can be obtained based on the position of an optical image of the light L irradiated onto the region E, so that a relative height of the subject's upper to lower eyelids can be accurately detected.

Figure 15:
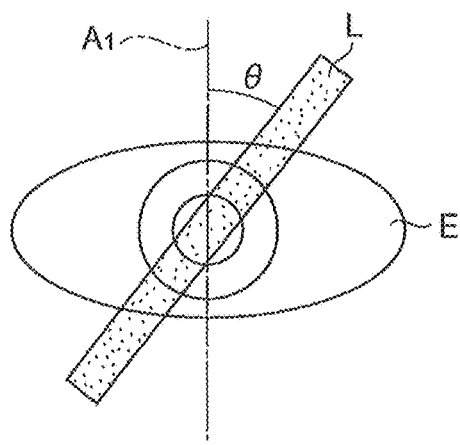
FIG. 15 shows front views when a light L is obliquely irradiated onto the subject's region E in a modification of the present invention.
Figure 15:
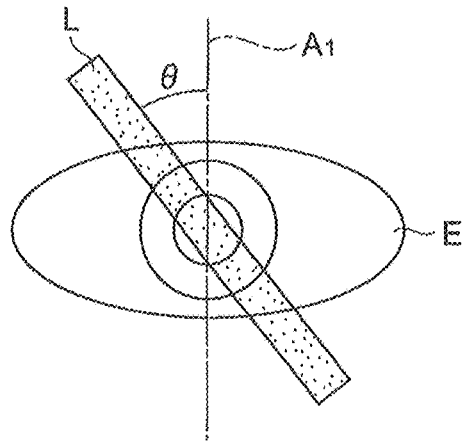
Figure 16:
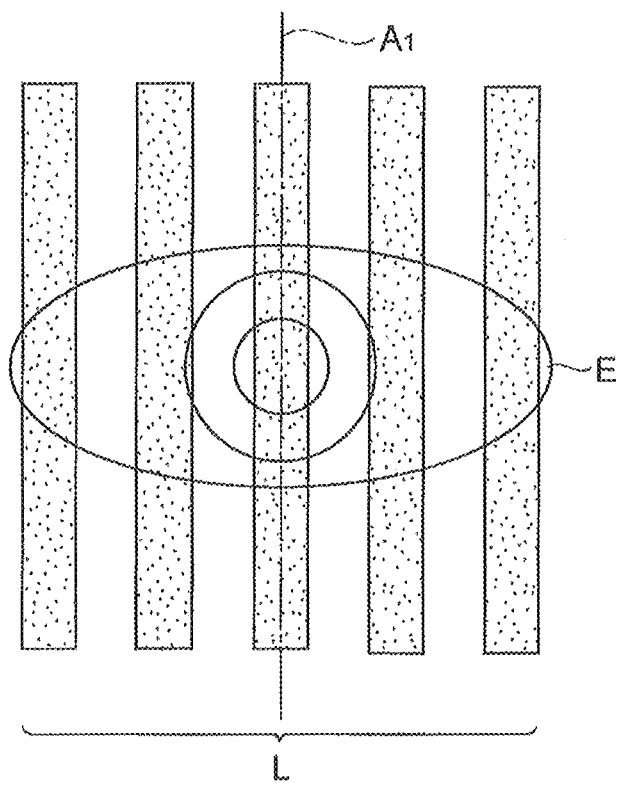
FIG. 16 is a front view when a plurality of lights L are irradiated onto the subject's region E in a modification of the present invention.

Also, the lighting device 1 is not limited to irradiating a single light L perpendicularly onto a subject's region E. FIG. 15 shows front views when a light L is obliquely irradiated onto the subject's region E. On the other hand, FIG. 16 is a front view when a plurality of lights L are irradiated onto the subject's region E. As shown in the parts (a) and (b) of FIG. 14, the light L may be irradiated in a manner rotated clockwise or counterclockwise by a predetermined angle θ onto the region E, or as shown in FIG. 16, may be irradiated as a plurality of lights at arbitrary intervals onto the region E. Also, the two methods shown in FIG. 15 and FIG. 16 may be combined. In either case, accurately measuring becomes possible even when the subject moves during measurement or when there is the influence of a skin condition of an irradiation site, eyelashes, etc. Also, it suffices that light irradiated from the lighting device 1 extends across the upper eyelid $E_u$ to the lower eyelid $E_d$, and it is not necessary to extend so as to include the whole of the pupil $E_p$, the sclera (white) $E_s$, and the iris $E_i$.

Here, in the above measurement apparatus, it is preferable that the arithmetic section obtains the height information based on the position of an optical image in a direction perpendicular to a direction in which the optical image extends. In this manner, a relative height of the subject's upper to lower eyelids is accurately detected, and an eyelid position can as a result be measured more precisely.

The lighting section may be disposed so as to directly oppose the subject, and the imaging device may have an optical axis on a plane for which a plane along the optical axis of light is rotated by a predetermined angle from a directly opposite direction to the subject. Also, the imaging device may be disposed so as to directly oppose the subject, and the lighting section may be constructed so that a plane including the optical axis comes on a plane for which a plane including a directly opposite direction to the subject is rotated by a predetermined angle. Further, the imaging device and the lighting section may be disposed so as to be obliquely directed with respect to the subject. In either case, a relative height of the subject's upper to lower eyelids can be accurately detected.

INDUSTRIAL APPLICABILITY

The present invention is used for application of a measurement apparatus and a measurement method for measuring a subject's eyelid position, and enables more precisely measuring the subject's eyelid position.

REFERENCE SIGNS LIST

1 . . . lighting device (lighting section); 2 . . . image measurement device; 6 . . . image sensor (imaging device); 7 . . . image operation section (arithmetic section); 10, 10A, 10B . . . eyeblink measurement system; E . . . region; Ia . . . imaging optical axis; L . . . light; La . . . irradiation optical axis.

The invention claimed is:
1. A measurement apparatus for measuring a subject's eyelid position, comprising:
  a lighting device configured to irradiate band-like linear light extending across the subject's upper to lower eyelids;
  an imaging device having an optical axis on a plane for which a plane including an extending bundle of rays of the light is rotated by a predetermined angle around an axis along a direction in which the band-like linear light extends across the subject's upper and lower eyelids; and
  at least one processor having instructions stored in a non-transitory memory device, that, when executed by the at least one processor, cause the measurement apparatus to perform operations comprising:

obtaining height information indicating a height in the direction of irradiation of the light, based on a position of an optical image in an image imaged by the imaging device, and measuring the eyelid position based on the height information, wherein the height information is obtained based on the position of an optical image in a direction perpendicular to a direction in which the optical image extends, wherein the imaging device is configured to capture the image including a first scattered light image of the subject's eyelid and a second scattered light image of the subject's sclera, and the at least one processor causes the measurement apparatus to obtain height information indicating a height in the direction of irradiation of the light, based on a horizontal shift amount between a position of the first scattered light image and a position of the second scattered light image in the direction perpendicular to the direction in which the optical image extends.

2. The measurement apparatus according to claim 1, wherein the lighting device is disposed so as to directly oppose the subject, and the imaging device has an optical axis on a plane for which a plane along the optical axis of light is rotated by a predetermined angle from a directly opposite direction to the subject.

3. The measurement apparatus according to claim 1, wherein the imaging device is disposed so as to directly oppose the subject, and the lighting device is constructed so that a plane including the optical axis comes on a plane for which a plane including a directly opposite direction to the subject is rotated by the predetermined angle.

4. The measurement apparatus according to claim 1, wherein the imaging device and the lighting device are disposed so as to be obliquely directed with respect to the subject.

5. A measurement method for measuring a subject's eyelid position, comprising:

an illuminating step of irradiating band-like linear light extending across the subject's upper to lower eyelids;

an imaging step of setting an imaging optical axis on a plane for which a plane including an extending bundle of rays of the light is rotated by a predetermined angle around an axis along a direction in which the band-like linear light extends across the subject's upper and lower eyelids, and obtaining an image of the subject; and an arithmetic step of obtaining height information indicating a height in the direction of irradiation of the light, based on a position of an optical image in the image obtained in the imaging step, and measuring the eyelid position based on the height information, wherein the height information is obtained based on the position of an optical image in a direction perpendicular to a direction in which the optical image extends, obtaining the image of the subject includes obtaining a first scattered light image of the subject's eyelid and a second scattered light image of the subject's sclera, and obtaining the height information indicating the height in the direction of irradiation of the light is based on a horizontal shift amount between a position of the first scattered light image and a position of the second scattered light image in the direction perpendicular to the direction in which the optical image extends.

* * * * *